United States Patent
Sandstrom et al.

(10) Patent No.: US 10,219,896 B2
(45) Date of Patent: Mar. 5, 2019

(54) SEGMENTED TRANSCATHETER VALVE PROSTHESIS HAVING AN UNSUPPORTED VALVE SEGMENT

(71) Applicant: Medtronic, Inc., Minneapolis, MN (US)

(72) Inventors: Jeffrey Sandstrom, Scandia, MN (US); Alaena Maiorano, Fullerton, CA (US); Joel Racchini, Edina, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 15/609,106

(22) Filed: May 31, 2017

(65) Prior Publication Data
US 2017/0265998 A1  Sep. 21, 2017

Related U.S. Application Data

(63) Continuation of application No. 14/556,484, filed on Dec. 1, 2014, now Pat. No. 9,693,860.

(51) Int. Cl.
| | | |
|---|---|---|
| A61F 2/24 | (2006.01) | |
| A61F 2/07 | (2013.01) | |
| A61F 2/82 | (2013.01) | |

(52) U.S. Cl.
CPC .......... *A61F 2/2418* (2013.01); *A61F 2/2412* (2013.01); *A61F 2/07* (2013.01);
(Continued)

(58) Field of Classification Search
CPC ........ A61F 2/07; A61F 2/2418; A61F 2/2475; A61F 2/2412; A61F 2002/072; A61F 2002/075
See application file for complete search history.

(56) References Cited

U.S. PATENT DOCUMENTS

| 5,836,966 A | 11/1998 | St. Germain |
|---|---|---|
| 5,957,949 A | 9/1999 | Leonhardt et al. |

(Continued)

FOREIGN PATENT DOCUMENTS

WO  WO2013/078497  6/2013

OTHER PUBLICATIONS

PCT/US2015/063015, The International Search Report and The Written Opinion of the International Searching Authority, dated Mar. 1, 2016.

*Primary Examiner* — Dinah Baria
(74) *Attorney, Agent, or Firm* — Medler Ferro Woodhouse & Mills PLLC

(57) ABSTRACT

Embodiments hereof relate to a transcatheter valve prosthesis including a tubular fabric body, a first or inflow tubular scaffold attached to a first end portion of the tubular fabric body, and a second or outflow tubular scaffold attached to a second end portion of the tubular fabric body. A prosthetic valve component is disposed within and secured to an intermediate portion of the tubular fabric body that longitudinally extends between the first and second end portions of the tubular fabric body. The intermediate portion is unsupported such that neither of the first and second tubular scaffolds surrounds the intermediate portion of the tubular fabric body. The intermediate portion may include one or more windows for coronary access and may include one or more commissure reinforcement members coupled thereto to provide support for the prosthetic valve component.

14 Claims, 13 Drawing Sheets

(52) U.S. Cl.
CPC ............... *A61F 2/24* (2013.01); *A61F 2/2436* (2013.01); *A61F 2002/828* (2013.01); *A61F 2210/0014* (2013.01); *A61F 2220/0016* (2013.01); *A61F 2220/0075* (2013.01); *A61F 2230/008* (2013.01); *A61F 2230/0054* (2013.01); *A61F 2230/0067* (2013.01); *A61F 2250/0039* (2013.01)

(56) References Cited

U.S. PATENT DOCUMENTS

| | | |
|---|---|---|
| 7,070,616 B2 | 7/2006 | Majercak |
| 8,721,713 B2 | 5/2014 | Tower et al. |
| 2003/0199971 A1 | 10/2003 | Tower et al. |
| 2004/0082989 A1 | 4/2004 | Cook |
| 2006/0020333 A1 | 1/2006 | Lashinski et al. |
| 2006/0217802 A1 | 9/2006 | Ruiz |
| 2009/0276040 A1 | 11/2009 | Rowe |
| 2011/0245917 A1 | 10/2011 | Savage et al. |
| 2011/0251675 A1 | 10/2011 | Dwork |
| 2011/0251681 A1 | 10/2011 | Shipley et al. |
| 2011/0251682 A1 | 10/2011 | Murray, III et al. |
| 2011/0264202 A1 | 10/2011 | Murray, III et al. |
| 2013/0053944 A1 | 2/2013 | Welch |
| 2013/0131788 A1 | 5/2013 | Quadri |
| 2013/0172984 A1 | 7/2013 | Greenberg |

SEGMENTED TRANSCATHETER VALVE PROSTHESIS HAVING AN UNSUPPORTED VALVE SEGMENT

RELATED APPLICATIONS

This application is a continuation of U.S. application Ser. No. 14/556,484, filed Dec. 1, 2014, now allowed, the disclosure of which is incorporated by reference herein in its entirety.

FIELD OF THE INVENTION

The invention relates in general to valve prostheses and more particularly to a valve prosthesis for transcatheter delivery.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis, in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, flexible prosthetic valves supported by stent or scaffold structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by compressing onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al. entitled "Percutaneous Placement Valve Stent", which is incorporated by reference herein in its entirety. Another example of a stented prosthetic valve for a percutaneous pulmonary valve replacement procedure is described in U.S. Patent Application Publication No. 2003/0199971 A1 and U.S. Pat. No. 8,721,713, both filed by Tower et al., each of which is incorporated by reference herein in its entirety.

Although transcatheter delivery methods have provided safer and less invasive methods for replacing a defective native heart valve, complications may arise including vessel trauma due to percutaneous delivery within highly curved anatomy and/or due to a large delivery profile of the prosthesis, inaccurate placement of the valve prosthesis, conduction disturbances, coronary artery obstruction, and/or undesirable paravalvular leakage and/or regurgitation at the implantation site. Embodiments hereof are directed to a valve prosthesis having an improved configuration to address one or more of the afore-mentioned complications.

BRIEF SUMMARY OF THE INVENTION

Embodiments hereof relate to a transcatheter valve prosthesis including a tubular fabric body formed from a synthetic material, the tubular fabric body having opposing first and second end portions and an intermediate portion extending between the first and second end portions. A first tubular scaffold is attached to the tubular fabric body along the first end portion thereof. A second tubular scaffold is attached to the tubular fabric body along the second end portion thereof. The first and second tubular scaffolds are independent from each other. A prosthetic valve component is disposed within and secured to the intermediate portion of the tubular fabric body. The intermediate portion of the tubular fabric body is unsupported such that neither of the first or second tubular scaffolds surround the intermediate portion of the tubular fabric body. The prosthesis has a compressed configuration for percutaneous delivery within a vasculature and an expanded configuration for deployment within a native valve.

Embodiments hereof also relate to a transcatheter valve prosthesis including a tubular fabric body having a first end portion, a second end portion, and an intermediate portion that longitudinally extends between the first and second end portions. A first tubular scaffold is attached to the tubular fabric body along the first end portion thereof. A second tubular scaffold is attached to the tubular fabric body along the second end portion thereof. The first and second tubular scaffolds are configured to be self-expanding and are sized to deploy against native valve tissue. In addition, the first and second tubular scaffolds are independent from each other. A prosthetic valve component is disposed within and secured to the intermediate portion of the tubular fabric body. The prosthetic valve component includes three leaflets. Three reinforcement members are attached to the intermediate portion of the tubular fabric body, the three reinforcement members being aligned with commissures of the three leaflets of the prosthetic valve component. The intermediate portion of the tubular fabric body is unsupported such that neither of the first or second tubular scaffolds surround the intermediate portion of the tubular fabric body and only the three reinforcement members are coupled to the intermediate portion. The prosthesis has a compressed configuration for percutaneous delivery within a vasculature and an expanded configuration for deployment within a native valve.

Embodiments hereof also relate to a segmented transcatheter valve prosthesis including a tubular fabric body formed from a synthetic material, a first tubular scaffold attached to the tubular fabric body along a first end portion thereof such that the first tubular scaffold and the first end portion form a first anchoring segment at an inflow end of the prosthesis, and a second tubular scaffold attached to the tubular fabric body along a second end portion thereof such that the second tubular scaffold and the second end portion form a second anchoring segment at an outflow end of the prosthesis. The first and second tubular scaffolds are independent from each other. A prosthetic valve component is disposed within and secured to an intermediate portion of the tubular fabric body that extends between the first and second end portions of the tubular fabric body, the prosthetic valve component and intermediate portion forming a central valve segment of the prosthesis. The central valve segment longitudinally extends between the first and second anchoring segments of the prosthesis and is unsupported such that neither of the first or second tubular scaffolds surround the intermediate portion of the tubular fabric body. The prosthesis has a compressed configuration for percutaneous delivery within a vasculature and an expanded configuration for deployment within a native valve.

Embodiments hereof also relate to a method of implanting a transcatheter valve prosthesis within a native valve. The method includes the step of percutaneously advancing a catheter to a target site, wherein the catheter includes a valve prosthesis in a compressed configuration mounted on a distal portion thereof. The prosthesis includes a tubular fabric body, a first tubular scaffold attached to a first end of the tubular fabric body, a second tubular scaffold attached to a second opposing end of the tubular fabric body, and a prosthetic valve component disposed within and secured to an intermediate portion of the tubular fabric body that longitudinally extends between the first and second tubular scaffolds. The first and second tubular scaffolds are configured to be self-expanding and are independent from each other. The intermediate portion of the tubular fabric body is unsupported such that neither of the first or second tubular scaffolds surrounds the tubular fabric body. An outer sheath of the catheter is retracted to expose the first tubular scaffold and the intermediate portion of the tubular fabric body, thereby deploying the first tubular scaffold. The catheter is proximally retracted in order to seat the first tubular scaffold against native valve tissue at the target site. The catheter is further proximally retracted in order to tension the intermediate portion of the tubular fabric body. The outer sheath of the catheter is further retracted to expose the second tubular scaffold, thereby deploying and anchoring the second tubular scaffold against tissue at the target site.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
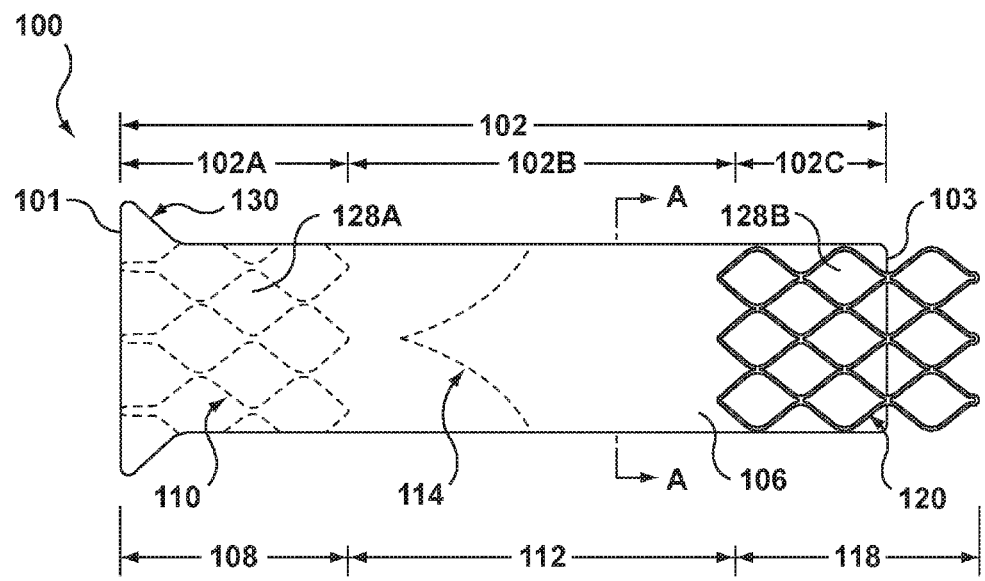
FIG. 1 is a side view of a segmented transcatheter valve prosthesis according to an embodiment hereof, wherein the valve prosthesis is in an expanded configuration.

Specific embodiments of the present invention are now described with reference to the figures, wherein like reference numbers indicate identical or functionally similar elements. Unless otherwise indicated, the terms "distal" and "proximal" are used in the following description with respect to a position or direction relative to the treating clinician. "Distal" and "distally" are positions distant from or in a direction away from the clinician, and "proximal" and "proximally" are positions near or in a direction toward the clinician. In addition, the term "self-expanding" is used in the following description with reference to one or more support structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include a pseudo-elastic metal such as a nickel titanium alloy or nitinol, a spring-tempered steel, various polymers, or a so-called super alloy, which may have a base metal of nickel, cobalt, chromium, or other metal. Mechanical memory may be imparted to a wire or scaffold structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and polycyclooctene can be used separately or in conjunction with other shape memory polymers.

The following detailed description is merely exemplary in nature and is not intended to limit the invention or the application and uses of the invention. Although the description of the invention is in the context of replacement of aortic valves, the prosthetic valves of the invention can also be used in other areas of the body, such as for replacement of a native mitral valve, for replacement of a native pulmonic valve, for replacement of a native tricuspid valve, for use as a venous valve, or for replacement of a failed previously-implanted prosthesis. Furthermore, there is no intention to be bound by any expressed or implied theory presented in the preceding technical field, background, brief summary or the following detailed description.

Embodiments hereof relate to a transcatheter valve prosthesis that has distinct longitudinally-extending segments including two anchoring segments at inflow and outflow ends of the prosthesis that are separated and connected by a central valve segment that extends therebetween. The transcatheter valve prosthesis includes a tubular fabric body and first and second scaffold or stent-like structures that are independent of each other, wherein each of the anchoring segments is comprised of one of the first and second scaffolds and a first or second end portion of the tubular fabric body and wherein the central valve segment is an unsupported intermediate portion of the tubular fabric body that extends between the anchoring segments and that houses a prosthetic valve component therein.

More particularly, with reference to FIG. 1, embodiments hereof relate to a transcatheter valve prosthesis 100 is comprised of three longitudinally-extending segments including a first anchoring segment 108, a second anchoring segment 118, and a central valve segment 112 that extends between first and second anchoring segments 108, 118. When configured as a replacement for an aortic valve, first anchoring segment 108 functions as an inflow end of valve prosthesis 100 and extends into and anchors within the aortic annulus of a patient's left ventricle, while second anchoring segment 118 functions as an outflow end of valve prosthesis 100 and is positioned in the patient's ascending aorta. "Inflow" and "outflow" refers to the direction of blood flow relative to the valve prosthesis once it is implanted in a patient. The length of each segment, i.e., first anchoring segment 108, central valve segment 112, and a second anchoring segment 118, may vary depending on the desired application, on the desired native valve location for the prosthesis, and/or on the size of the patient. In an embodiment hereof, when valve prosthesis 100 is in the expanded configuration, each segment is approximately a respective third of a total length of the prosthesis.

Transcatheter valve prosthesis 100 includes a tubular fabric body 102 formed from a synthetic material, the tubular fabric body having a first end 101 and a second or opposing end 103. Tubular fabric body 102 includes a first end portion 102A, a second end portion 102C, and an intermediate portion 102B that extends between first and second end portions 102A, 102C. Tubular fabric body 102 is a synthetic graft material shaped as a tubular body that defines a lumen 104 there-through as shown in the cross-sectional view of FIG. 1A. More particularly, tubular fabric body 102 is constructed from a suitable biocompatible material such as a low-porosity fabric, such as polyester, DACRON®, or polytetrafluoroethylene (PTFE). Tubular fabric body 102 is thin-walled so that valve prosthesis 100 may be compressed into a small diameter, yet is capable of acting as a strong, leak-resistant fluid conduit when expanded to a cylindrical tubular form. In one embodiment, tubular fabric body 102 may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example.

Transcatheter valve prosthesis 100 also includes first and second scaffold or stent-like structures 110, 120, respectively, that are independent of each other. "Independent" as used herein means that first and second tubular scaffolds are separate from each other and are not directly attached to each other. However, first and second tubular scaffolds 110, 120 are connected or indirectly linked to each other via central valve segment 112 that extends therebetween. First or inflow tubular scaffold 110 is attached to tubular fabric body 102 along first end portion 102A such that first tubular scaffold 110 and first end portion 102A form first anchoring segment 108 of prosthesis 100. Similarly, second or outflow tubular scaffold 120 is attached to tubular fabric body 102 along second end portion 102C such that second tubular scaffold 120 and second end portion 102C form second anchoring segment 118 of prosthesis 100. A prosthetic valve component 114 is disposed within and secured to intermediate portion 102B of tubular fabric body 102 such that prosthetic valve component 114 and intermediate portion 102B form central valve segment 112 of prosthesis 100. Central valve segment 112 of prosthesis 100 longitudinally extends between first and second anchoring segments 108, 118 and is unsupported or scaffold-free such that neither of first or second tubular scaffolds 110, 120 surround intermediate portion 102B of tubular fabric body 102 as will be described in more detail herein.

More particularly, first and second tubular scaffolds 110, 120 are coupled to first and second end portions 102A, 102C, respectively, of tubular fabric body 102 in order to bias and/or anchor the first and second end portions of tubular fabric body 102 into apposition with an interior wall of a body lumen (not shown). First and second end portions 102A, 102C, respectively, of tubular fabric body 102 are thus supported by first and second tubular scaffolds 110, 120. As used herein, "supported" means that the graft material of first and second end portions 102A, 102C of tubular fabric body 102 has radial support along its length and circumference. In particular, first tubular scaffold 110 surrounds and overlaps with first end portion 102A of tubular fabric body 102 and second tubular scaffold 120 surrounds and overlaps with second end portion 102C of tubular fabric body. First and second tubular scaffolds 110, 120 may longitudinally extend up to or beyond first and second ends 101, 103, respectively, of tubular fabric body 102. FIG. 1 illustrates an embodiment in which first tubular scaffold 110 longitudinally extends up to first end 101 of tubular fabric body 102, while second tubular scaffold 120 longitudinally extends beyond second end 103 of tubular fabric body 102. Alternatively, in another embodiment (now shown), first tubular scaffold 110 may longitudinally extend beyond first end 101 of tubular fabric body 102 and/or second tubular scaffold 120 may longitudinally extend up to second end 103 of tubular fabric body 102. First and second tubular scaffolds 110, 120 may be attached or mechanically coupled to first and second end portions 102A, 102C, respectively, of tubular fabric body 102 by various means, such as, for example, by stitching or suturing onto either an inner surface 107 (see FIG. 1A) or an outer surface 106 of tubular fabric body 102. FIG. 1 illustrates an embodiment in which first tubular scaffold 110 is coupled to inner surface 107 of tubular fabric body 102, while second tubular scaffold 120 is coupled to outer surface 106 of tubular fabric body 102. Alternatively, in another embodiment (now shown), first tubular scaffold 110 is coupled to outer surface 106 of tubular fabric body 102 and/or second tubular scaffold 120 is coupled to inner surface 107 of tubular fabric body 102.

Conversely, intermediate portion 102B of tubular fabric body 102 is scaffold-free and unsupported. "Unsupported" as used herein means that the graft material of intermediate portion 102B of tubular fabric body 102 has no radial support along its length or circumference and is not surrounded by any tubular or annular scaffold or stent-like structure. In particular, first and second tubular scaffolds 110, 120 do not surround and do not overlap intermediate portion 102B of tubular fabric body 102. As such, intermediate portion 102B is relatively flexible permitting delivery of the prosthesis in a highly curved anatomy and reducing stresses on valve prosthesis 100. Valve prosthesis 100 having unsupported intermediate portion 102B is particularly advantageous for delivery through a highly curved anatomy, such as the aortic arch. When valve prosthesis 100 is collapsed or compressed for delivery thereof, the segmented configuration of valve prosthesis 100 allows easier traversing through a highly curved anatomy since anchoring segments 108, 118 (which include first and second tubular scaffolds 110, 120) are relatively short and are separated from each other by central valve segment 112 (which includes unsupported intermediate portion 102B of tubular fabric body 102).

As previously mentioned, prosthetic valve component 114 is disposed within and secured to intermediate portion 102B of tubular fabric body 102. Since prosthetic valve component 114 is disposed within and secured to unsupported intermediate portion 102B which does not include any tubular or annular scaffolds coupled thereto, valve prosthesis 100 has a lower delivery or collapsed profile than a conventional prosthesis in which the single scaffold extends from a proximal end to a distal end of the prosthesis because prosthetic valve component 114 is surrounded by only graft material without further support structures, such as tubular scaffolds, that would add to the delivery profile. In an embodiment hereof, valve prosthesis 100 in a compressed configuration has a profile between 8 and 14 French, depending upon the type and thickness of the graft material utilized, when disposed within a catheter for percutaneous delivery thereof.

Figures 1A, 2:
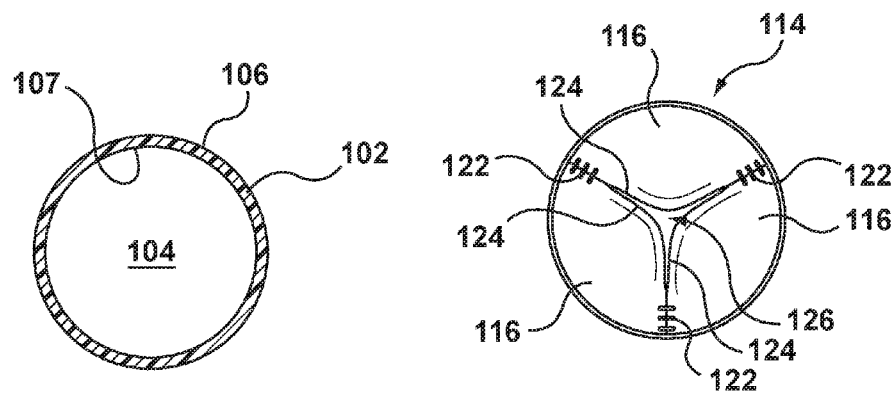
FIG. 1A is a cross-sectional view taken along line A-A of FIG. 1.
FIG. 2 is an end view of the valve prosthesis of FIG. 1, taken from the second or outflow end of the prosthesis.

Prosthetic valve component 114 is capable of blocking flow in one direction to regulate flow there-through via valve leaflets 116 that may form a bicuspid or tricuspid replacement valve. FIG. 2 is an end view of FIG. 1 taken from the second or outflow end of the prosthesis and illustrates an exemplary tricuspid valve having three leaflets 116, although a bicuspid leaflet configuration may alternatively be used in embodiments hereof. More particularly, if valve prosthesis 100 is configured for placement within a native valve having three leaflets such as the aortic, tricuspid, or pulmonary valves, valve prosthesis 100 includes three valve leaflets 116 although the valve prosthesis is not required to have the same number of leaflets as the native valve. If valve prosthesis 100 is configured for placement within a native valve having two leaflets such as the mitral valve, valve prosthesis 100 includes two or three valve leaflets 116. Valve leaflets 116 are sutured or otherwise securely and sealingly attached to the inner surface of intermediate portion 102B of tubular fabric body 102. Referring to FIG. 2, leaflets 116 are attached along their bases to inner surface 107 of intermediate portion 102B of tubular fabric body 102, for example, using sutures or a suitable biocompatible adhesive. Adjoining pairs of leaflets are attached to one another at their lateral ends to form commissures 122, with free edges 124 of the leaflets forming coaptation edges that meet in area of coaptation 126.

Leaflets 116 may be made of pericardial material; however, the leaflets may instead be made of another material. Natural tissue for replacement valve leaflets may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. Synthetic materials suitable for use as leaflets 116 include DACRON® commercially available from Invista North America S.A.R.L. of Wilmington, Del., other cloth materials, nylon blends, and polymeric materials. One polymeric material from which the leaflets can be made is an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue.

Figure 3:
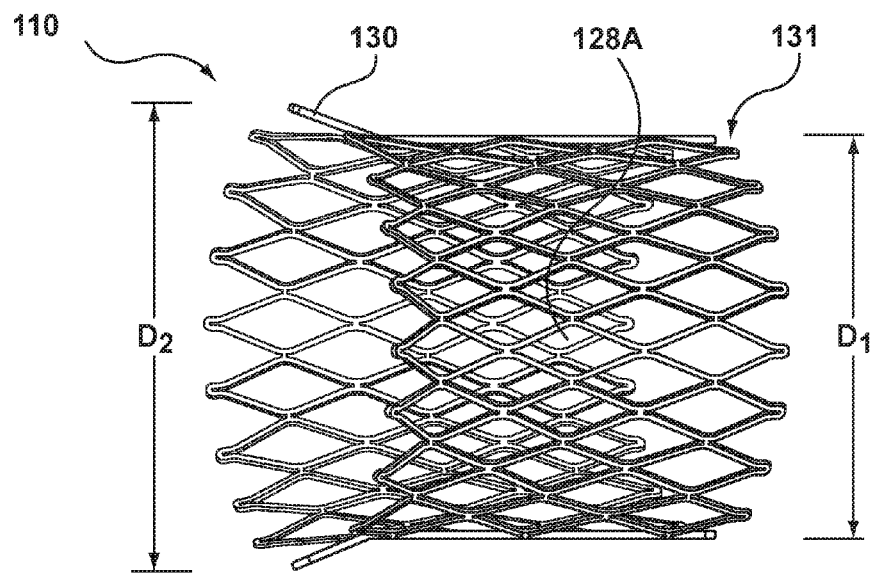
FIG. 3 is a perspective view of a first tubular scaffold of the valve prosthesis of FIG. 1, wherein the first tubular scaffold is removed from the valve prosthesis of FIG. 1 for illustrative purposes only and is shown in an expanded configuration.
Figure 6:
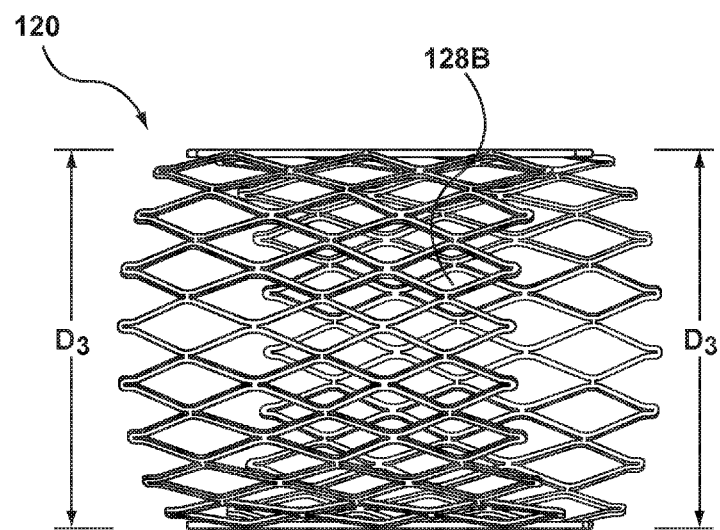
FIG. 6 is a perspective view of a second tubular scaffold of the valve prosthesis of FIG. 1, wherein the second tubular scaffold is removed from the valve prosthesis of FIG. 1 for illustrative purposes only and is shown in an expanded configuration.

First and second tubular scaffolds 110, 120 are shown removed from valve prosthesis 100 for illustrative purposes only in FIG. 3 and FIG. 6, respectively. First and second tubular scaffolds 110, 120 are both self-expanding components that return to an expanded deployed state from a compressed or constricted delivery state. First and second tubular scaffolds 110, 120 are both sized to anchor valve prosthesis 100 against native valve tissue when the prosthesis is in the expanded configuration. In this embodiment, first and second tubular scaffolds 110, 120 are tubular components having diamond-shaped openings 128A, 128B, respectively, which may be formed by a laser-cut manufacturing method and/or another conventional stent/scaffold forming method as would be understood by one of ordinary skill in the art. However, it will be understood by one of ordinary skill in the art that the illustrated configurations of first and second tubular scaffolds 110, 120 are exemplary and first and second tubular scaffolds 110, 120 may have alternative patterns or configurations. For example, in another embodiment (not shown), first and second tubular scaffolds 110, 120 may include one or more sinusoidal patterned rings coupled to each other to form a tubular component. In another embodiment hereof (not shown), the first and second tubular scaffolds are configured to be balloon-expandable rather than self-expanding and thus would not be required to be formed from a shape memory material.

Figure 4:
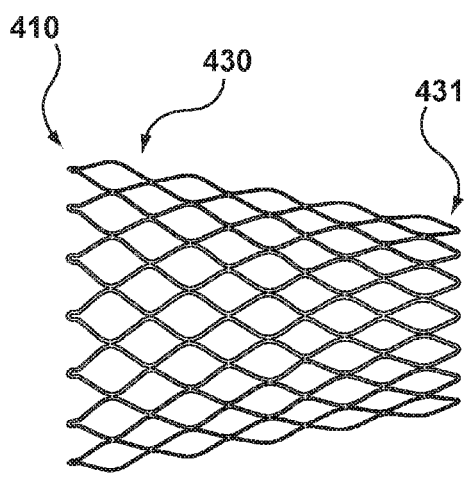
FIG. 4 is a side view of a first tubular scaffold according to another embodiment hereof, wherein the first tubular scaffold has an alternative flared end configuration and is shown in an expanded configuration.
Figure 5:
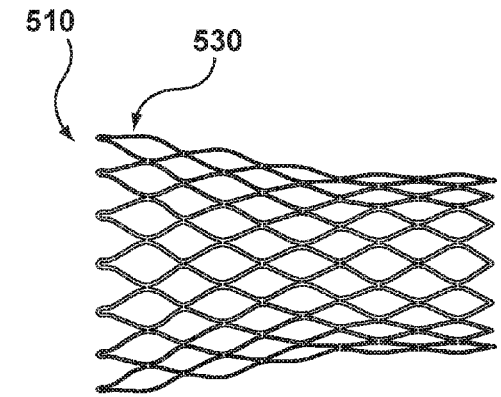
FIG. 5 is a side view of a first tubular scaffold according to another embodiment hereof, wherein the first tubular scaffold has an alternative flared end configuration and is shown in an expanded configuration.

First and second tubular scaffolds 110, 120 may each have distinct configurations and/or include an additional element that aids in fixing or anchoring valve prosthesis 100 within native valve anatomy. More particularly, with reference to FIG. 3, first tubular scaffold 110 is sized to extend into and anchor valve prosthesis 100 within the aortic annulus of a patient's left ventricle when valve prosthesis 100 is configured as a replacement for an aortic valve. As such, first tubular scaffold 110 includes a bulged or flared end 130 that is configured to seat valve prosthesis 100 within the aortic annulus, as described below with reference to FIGS. 14-18. The seating against the aortic annulus provides anatomical alignment by positioning and aligning valve prosthesis 100 at the proper depth and eliminating canting of the prosthesis, which is unintentional slanting or tilting of the prosthesis. As shown in FIG. 3, flared end 130 has a diameter $D_2$ which is larger than a diameter $D_1$ of an opposing end 131 of first tubular scaffold 110. The sizes of diameters $D_1$ and $D_2$ may vary according to a particular patient's anatomy and/or the intended native valve for replacement. In the embodiment of FIG. 3, flared end 130 longitudinally extends a relatively short distance compared to the entire length of first tubular scaffold 110. However, it will be understood by one of ordinary skill in the art that the illustrated configuration of flared end 130 is exemplary and the flared end of first tubular scaffolds 110 may have alternative patterns or configurations. For example, FIG. 4 and FIG. 5 illustrate alternative configurations of a flared end. A first tubular scaffold 410 of FIG. 4 includes a flared portion 430 which gradually tapers toward opposing end 431 and extends the entire length of the tubular scaffold. In addition, a first tubular scaffold 510 of FIG. 5 includes a flared end 530 which tapers and extends approximately half the length of the tubular scaffold. Further, the flared ends may have a generally curved outer surface or profile similar to the flared end configuration shown in FIG. 7.

With reference to FIG. 6, second tubular scaffold 120 is sized to extend into and anchor valve prosthesis 100 within the patient's ascending aorta when valve prosthesis 100 is configured as a replacement for an aortic valve. Second tubular scaffold 120 has a generally straight profile such that the opposing ends thereof each have a diameter $D_3$ as shown in FIG. 6. The size of diameter $D_3$ may vary according to a particular patient's anatomy. In another embodiment hereof, shown in FIG. 7, a second tubular scaffold 720 may include a bulged or flared end 730 to aid in fixation thereof to the aorta. Flared end 730 has a diameter $D_4$ which is larger than diameter $D_3$ of the opposing end of second tubular scaffold 720. When coupled to a tubular fabric body such as tubular fabric body 102 and used as an aortic valve prosthesis, second tubular scaffold 720 would be oriented such that flared end 730 forms the outflow end of the prosthesis.

Figures 7, 8:
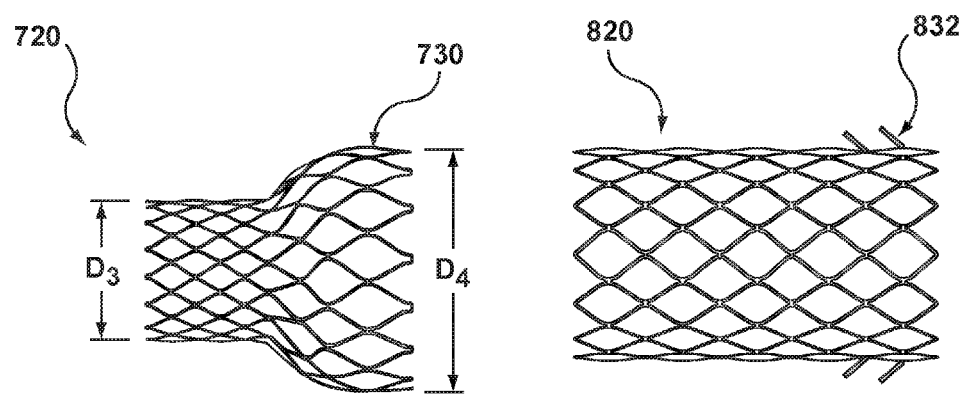
FIG. 7 is a side view of a second tubular scaffold according to another embodiment hereof, wherein the second tubular scaffold has a flared end configuration and is shown in an expanded configuration.
FIG. 8 is a side view of a second tubular scaffold according to another embodiment hereof, wherein the second tubular scaffold includes barbs and is shown in an expanded configuration.

In another embodiment hereof, shown in FIG. 8, a second tubular scaffold 820 may include a plurality of barbs 832 to aid in fixation thereof to the aorta. Barbs 832 radially extend away from second tubular scaffold 820, and each include a free end that is sharp enough to engage with tissue for implantation of the valve prosthesis. Barbs 832 extend at an acute angle relative to the outer surface of second tubular scaffold 820 so that they extend at least slightly outward relative to the outer surface of the tubular scaffold. Barbs 832 may be coupled to second tubular scaffold 820 or integrally formed therewith. When coupled to a tubular fabric body such as tubular fabric body 102 and used as an aortic valve prosthesis, second tubular scaffold 820 would be oriented such that barbs 832 are positioned at the outflow end of the prosthesis.

In addition to and/or as an alternative to the scaffold configurations or additional elements described above that aid in fixing or anchoring valve prosthesis 100 within native valve anatomy, second or outflow tubular scaffold 120 may be configured to exert a higher radial force than first or inflow tubular scaffold 110. As used herein, "radial force" includes both a radial force exerted during expansion/deployment as well as a chronic radial force continuously exerted after implantation such that a scaffold has a predetermined compliance or resistance as the surrounding native anatomy, i.e., the ascending aorta or the native valve annulus, expands and contracts during the cardiac cycle. First or inflow tubular scaffold 110 is configured to have a lower radial force in order to reduce the likelihood of conduction disturbances that may occur in the aortic annulus while second or outflow tubular scaffold 120 is configured to have a higher radial force in order to ensure that valve prosthesis 100 is anchored within the native valve anatomy. In order to configure the tubular scaffolds with differing relative radial forces, second or outflow tubular scaffold 120 may be constructed with relatively thicker and/or shorter segments of material that form diamond shaped openings 128B. Conversely, first or inflow tubular scaffold 110 may be constructed with relatively thinner and/or longer segments of material that form diamond shaped openings 128A. Shorter and/or thicker scaffold segments have less flexibility but greater radial force to ensure that second or outflow tubular scaffold 120 seals against the native anatomy. Other variations or modification of the tubular scaffolds may be used to configure the tubular scaffolds with differing relative radial forces without departing from the scope of the present invention.

Figure 9:
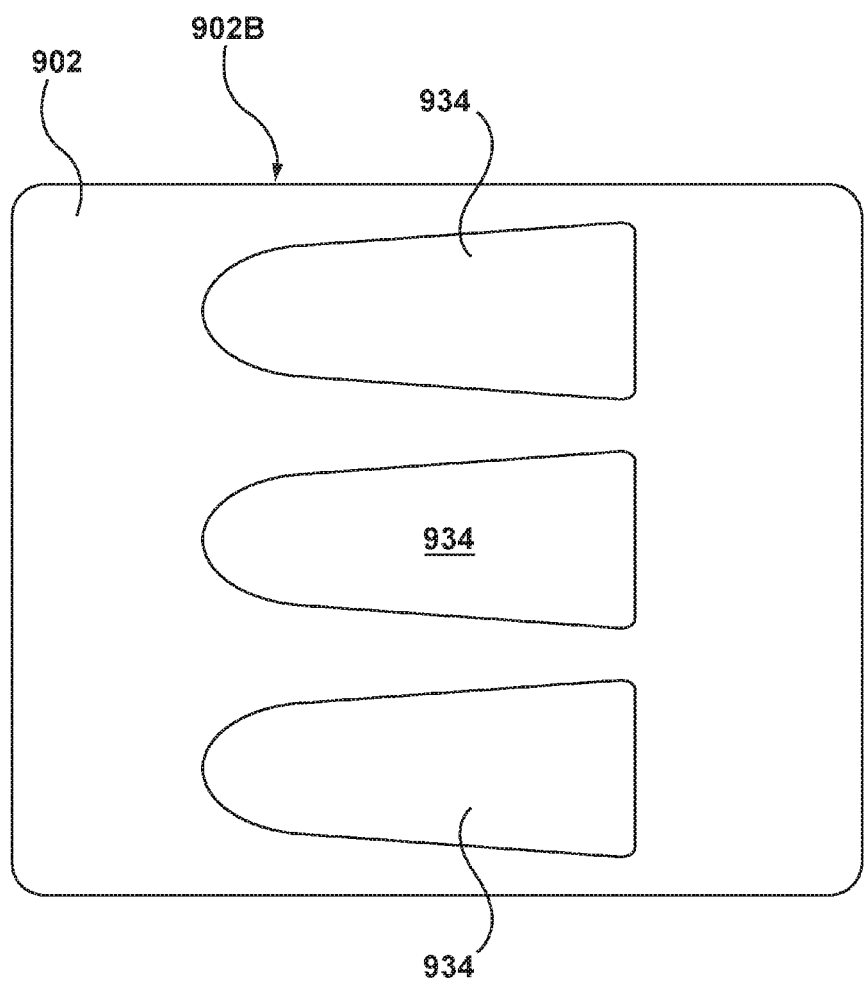
FIG. 9 depicts a tubular fabric body according to another embodiment hereof, wherein the tubular fabric body is cut in an axial direction and laid flat for illustrative purposes only and includes windows for coronary access formed there-though.

FIG. 9 illustrates another embodiment of a tubular fabric body 902 cut in an axial direction and laid flat for illustrative purposes only. Tubular fabric body 902 may include one or more windows or openings 934 formed there-through along unsupported intermediate portion 902B thereof in order to allow access to one or more coronary arteries. More particularly, in the aortic valve, the coronary arteries originate or branch from two of the three native valve sinuses. The left coronary artery originates from the left posterior aortic sinus, and the right coronary artery originates from the anterior aortic sinus. Usually, no vessels branch from the right posterior aortic sinus, which is therefore known as the non-coronary sinus. When valve prosthesis 100 is configured as a replacement for an aortic valve, windows 934 formed along unsupported intermediate portion 902B of tubular fabric body 902 increase perfusion and accessibility to the coronary arteries. Although tubular fabric body 902 is shown with three windows or openings 934 for positioning within each native valve sinus, tubular fabric body 902 may alternatively be provided with one or two openings. Windows 934 may be any shape, and advantageously may be of a relatively larger size than coronary access windows or openings formed on a conventional prosthesis in which the single scaffold extends from a proximal end to a distal end of the prosthesis. More particularly, coronary access openings formed on a conventional prosthesis in which the single scaffold extends from a proximal end to a distal end of the prosthesis are limited in size due to the scaffold or stent and the coronary access openings can be no larger than the openings of the single scaffold or stent of the prosthesis. Conversely, unsupported intermediate portion 902B of tubular fabric body 902 need only include enough material to couple a prosthetic valve component thereto, and as such windows 934 are of a relatively increased size or dimension that may extend between adjacent leaflets of the prosthetic valve component.

Figure 10:
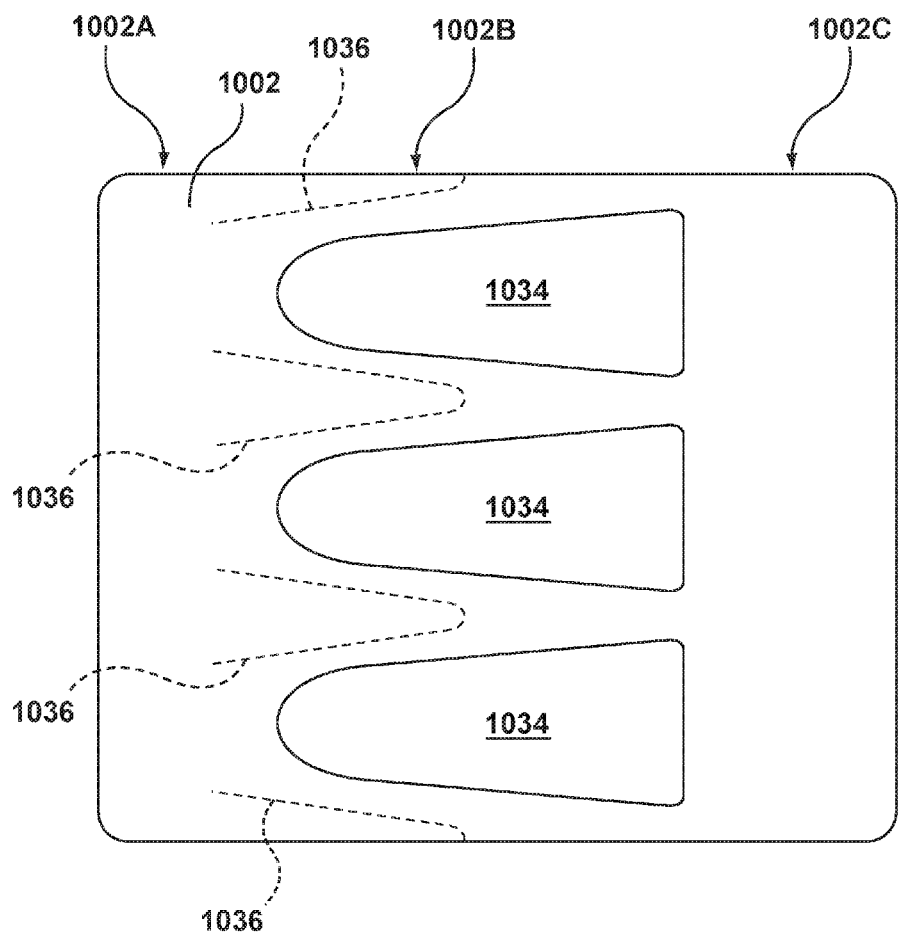
FIG. 10 depicts a tubular fabric body according to another embodiment hereof, wherein the tubular fabric body is cut in an axial direction and laid flat for illustrative purposes only and includes windows for coronary access formed there-though as well as commissure reinforcement members that extend between the windows in order to aid in valve alignment and coaptation.

FIG. 10 illustrates another embodiment of a tubular fabric body 1002 cut in an axial direction and laid flat for illustrative purposes only. Similar to tubular fabric body 902, tubular fabric body 1002 includes three windows or openings 1034 formed there-through along unsupported intermediate portion 1002B thereof in order to allow access to one or more coronary arteries. In addition to windows 1034, tubular fabric body 1002 includes three reinforcement members 1036 coupled to intermediate portion 1002B. Reinforcement members 1036 extend between windows 1034 and are aligned with commissures of the three leaflets of the prosthetic valve component (not shown). Reinforcement members 1036 serve to reinforce the graft material of unsupported intermediate portion 1002B around the commissures of the three leaflets of the prosthetic valve component in order to aid in valve alignment and coaptation. In the embodiment of FIG. 10, reinforcement members 1036 are generally U-shaped but it will be apparent to one of ordinary skill in the art that reinforcement members 1036 may be other configurations, including a linear configuration, a V-shaped configuration, or other configuration suitable for providing support to the three leaflets of the prosthetic valve component. FIG. 10 illustrates an embodiment in which reinforcement members 1036 are coupled to the inner surface of the tubular fabric body 102. However, reinforcement members 1036 may be attached or mechanically coupled to tubular fabric body 1002 by various means, such as, for example, by stitching or suturing onto either an inner surface or an outer surface of tubular fabric body 1002 or other methods of attachment including gluing and/or heat treatments to embed reinforcement members 1036 into tubular fabric body 1002. Reinforcement members 1036 may be formed from a metallic or polymeric material that is sufficiently rigid to provide support to the three leaflets of the prosthetic valve component such as but not limited to Nitinol, Cobalt-chromium, Platinum-Iridium, 316L Stainless Steel, Polyethylene, polyurethane, polypropolyne, or PEEK.

Figure 11:
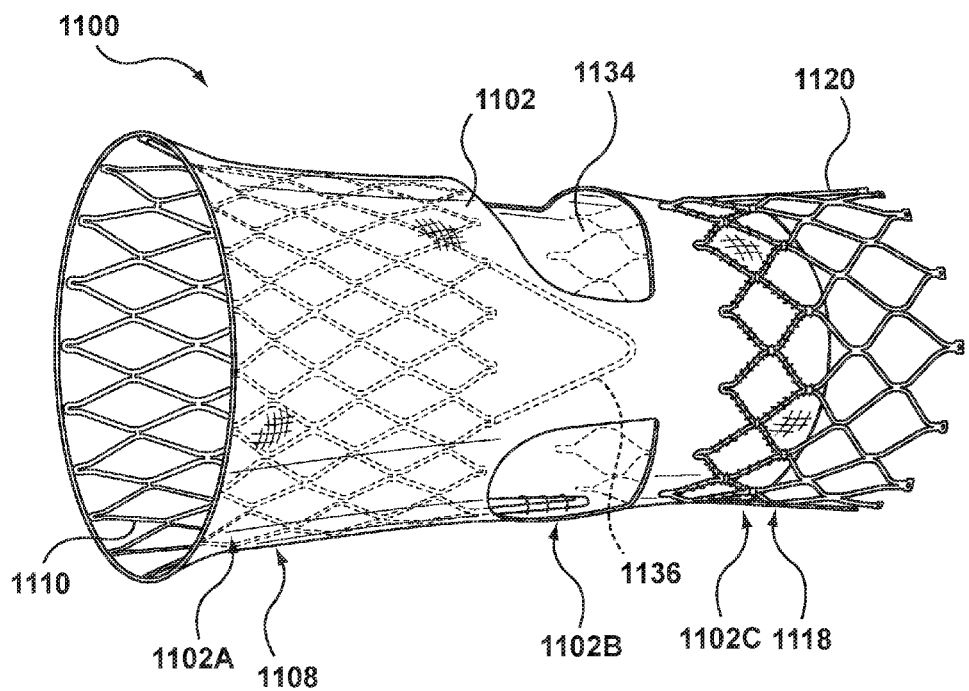
FIG. 11 is a perspective view of a valve prosthesis according to another embodiment hereof, wherein the valve prosthesis includes a first tubular scaffold having commissure reinforcement members that extend from the first tubular scaffold to aid in valve alignment and coaptation, wherein the valve prosthesis is shown in an expanded configuration.
Figure 12:
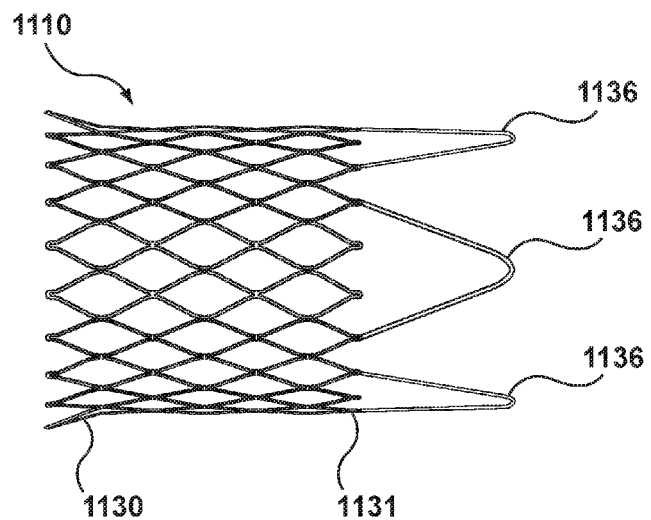
FIG. 12 is a side view of the first tubular scaffold of the valve prosthesis of FIG. 11, wherein the first tubular scaffold is removed from the valve prosthesis of FIG. 11 for illustrative purposes only and is shown in an expanded configuration.

Reinforcement members 1036 are individual components or elements that are attached to intermediate portion 1002B of tubular fabric body 1002 but not attached to each other. As such, reinforcement members 1036 are not configured to provide circumferential or radial support to unsupported intermediate portion 1002B of tubular fabric body 1002. Unlike first and second scaffolds (not shown in FIG. 10) that are to be coupled along first and second end portions 1002A, 1002C of tubular fabric body 1002, reinforcement members 1036 cannot be used as anchoring mechanisms because reinforcement members 1036 provide or exert no radial expansion force. In an embodiment hereof, reinforcement members 1036 are only attached to intermediate portion 1002B of tubular fabric body 1002 and are not attached to any other structure of the valve prosthesis. In another embodiment hereof, the reinforcement members may be coupled to or extend from the first tubular scaffold of the valve prosthesis. More particularly, FIGS. 11-12 illustrate an embodiment in which a valve prosthesis 1100 includes a first or inflow tubular scaffold 1110 having reinforcement members 1136 extending therefrom. Reinforcement members 1136 may be attached to first tubular scaffold 1110 or may be integrally formed therewith via a laser-cut manufacturing method. First tubular scaffold 1110 includes a flared end 1130, which forms the inflow end of the prosthesis, and reinforcement members 1136 are attached to or formed on opposing end 1131 of first tubular scaffold 1110. Valve prosthesis 1100 also includes a second or outflow tubular scaffold 1120. Similar to valve prosthesis 100, valve prosthesis 1100 includes a first anchoring segment 1108 that includes first tubular scaffold 1110 and first end portion 1102A of tubular fabric body 1102, a second anchoring segment 1118 that includes second tubular scaffold 1120 and second end portion 1102C of tubular fabric body 1102, and a central valve segment 1112 that includes intermediate portion 1102B of tubular fabric body and a prosthetic valve component (not shown in FIG. 11) that is disposed within and secured to intermediate portion 1102B of tubular fabric body 1102. Intermediate portion 1102B is unsupported such that neither of first or second tubular scaffolds 1110, 1120 surround the graft material thereof and only three reinforcement members 1136 are coupled thereto. Intermediate portion 1102B also includes three windows 1134 for coronary access.

Figure 13:
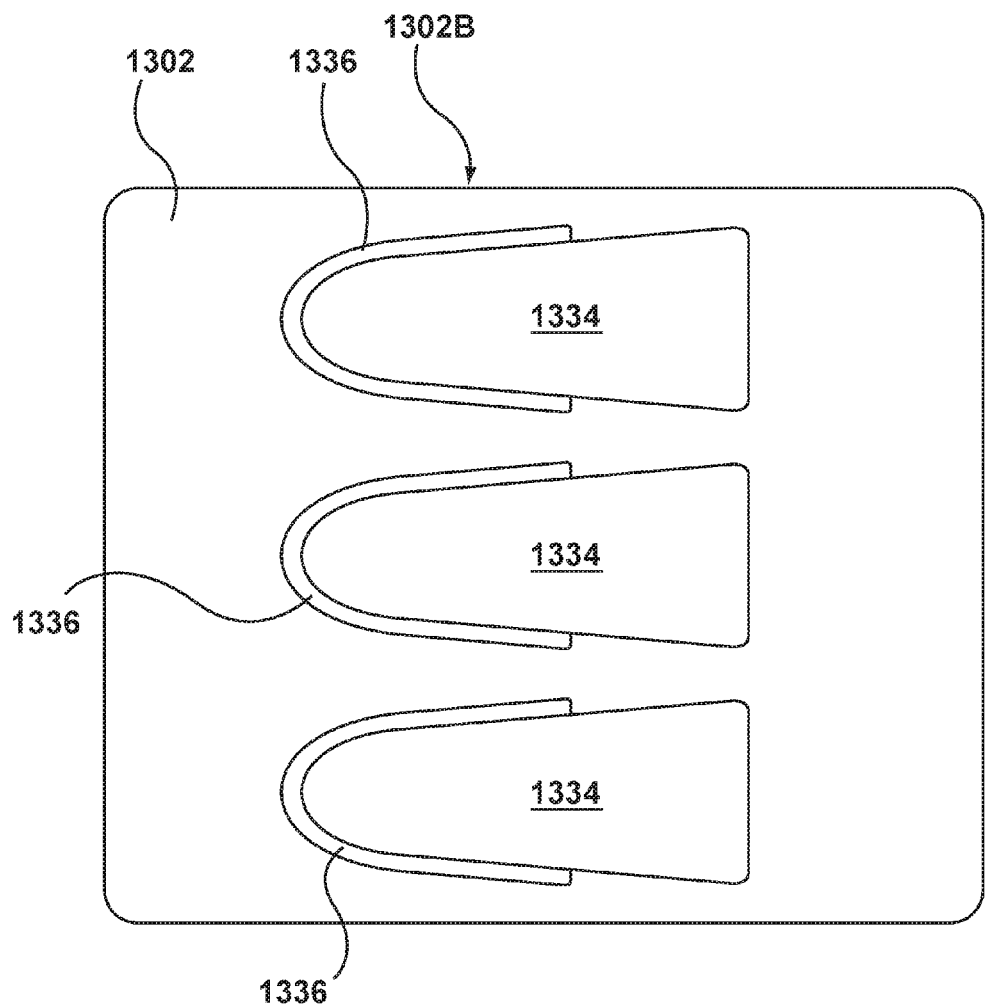
FIG. 13 depicts a tubular fabric body according to another embodiment hereof, wherein the tubular fabric body is laid flat for illustrative purposes only and includes windows for coronary access formed there-though as well as commissure reinforcement members formed from fabric that around the windows in order to aid in valve alignment and coaptation.

FIG. 13 illustrates another embodiment of a tubular fabric body 1302 laid flat out for illustrative purposes only. Similar to tubular fabric body 902, tubular fabric body 1302 includes three windows or openings 1334 formed there-through along unsupported intermediate portion 1302B thereof in order to allow access to one or more coronary arteries. In addition to windows 1334, tubular fabric body 1302 includes three reinforcement members 1336 coupled to intermediate portion 1302B. In this embodiment, reinforcement members 1336 are formed by attaching additional fabric material to at least a portion of the perimeters of windows 1334. In an embodiment, the additional fabric material may include extra folded fabric. In another embodiment, the additional fabric material may include a metallic or polymeric wire support element. Reinforcement members 1336 reinforce or strengthen the commissure region of the valve by shaping the leaflets and supporting the leaflets during opening and closing thereof, and thus provide more reliable leaflet coaptation. In addition to aiding in valve alignment and coaptation, reinforcement members 1336 reinforce or strengthen the perimeter of windows 1334.

Figure 14:
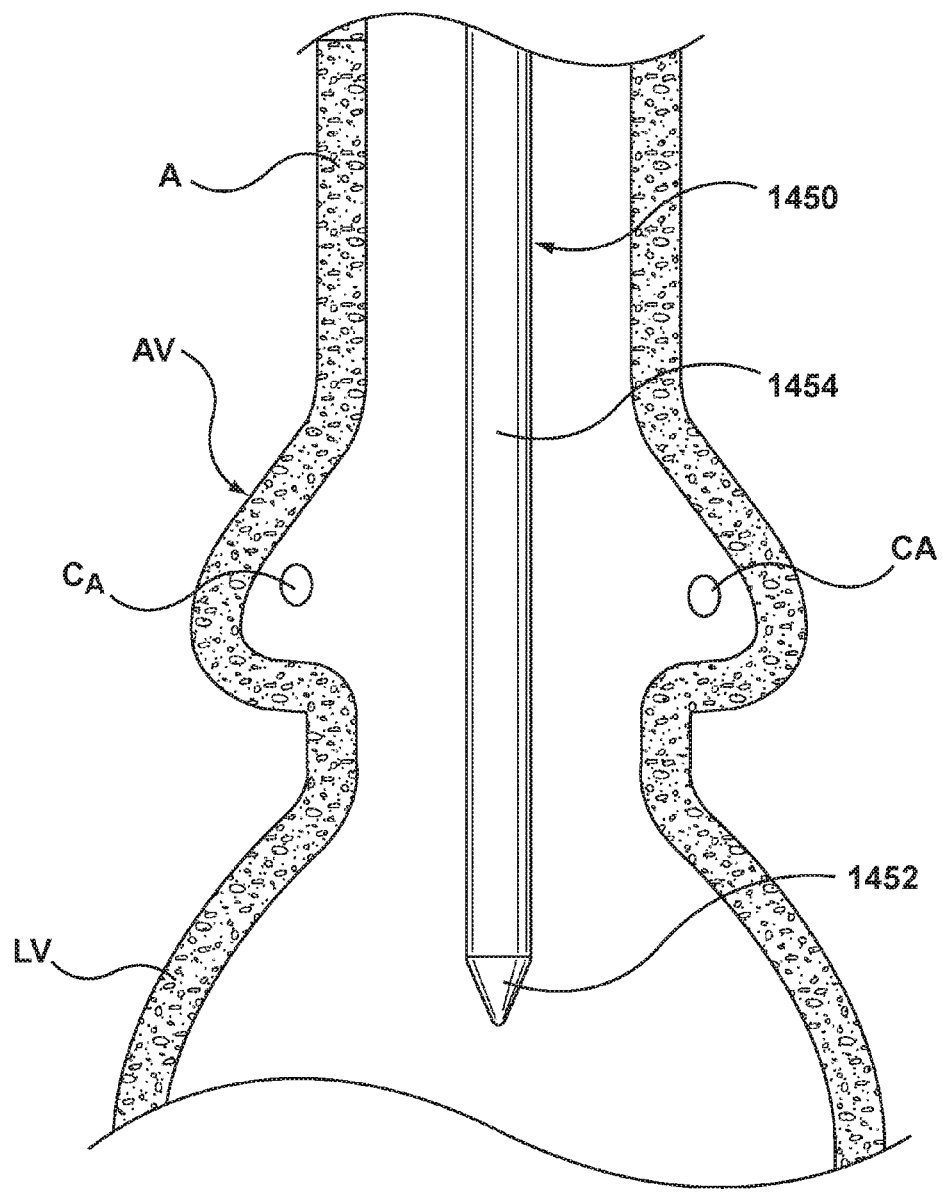
FIG. 14 depicts a step of a method for implanting the valve prosthesis of FIG. 1, wherein a catheter including the valve prosthesis is advanced to a native aortic valve treatment site.

FIGS. 14-18 illustrate an exemplary method of implanting the above-described transcatheter valve prosthesis 100 within a native valve according to an embodiment hereof. As will be understood by one of ordinary skill in the art, valve prosthesis 100 in a radially compressed configuration is loaded onto a distal portion of a catheter 1450. The radially compressed configuration of valve prosthesis 100 is suitable for percutaneous delivery within a vasculature. Catheter 1450 is configured for percutaneous transcatheter valve replacement, and may be one of, but is not limited to, the delivery systems described in U.S. Patent Publication No. 2011/0245917 to Savage et al., U.S. Patent Publication No. 2011/0251675 to Dwork, U.S. Patent Publication No. 2011/0251681 to Shipley et al., U.S. Patent Publication No. 2011/0251682 to Murray, III et al., and U.S. Patent Publication No. 2011/0264202 to Murray, III et al., each of which is herein incorporated by reference in its entirety. As shown in FIG. 14, in accordance with techniques known in the field of interventional cardiology and/or interventional radiology, catheter 1450 having distal end 1452 is transluminally advanced in a retrograde approach through the vasculature to the treatment site, which in this instance is a target diseased native aortic valve AV that extends between a patient's left ventricle LV and a patient's aorta A. The coronary arteries $C_A$ are also shown on the sectional view of FIG. 14. Delivery of catheter 1450 to the native aortic valve AV may be accomplished via a percutaneous transfemoral approach or may be positioned within the desired area of the heart via different delivery methods known in the art for accessing heart valves. During delivery, valve prosthesis 100 remains compressed within an outer sheath 1454 of catheter 1450. Catheter 1450 is advanced until distal end 1452 is distal to the native aortic valve AV and disposed within the left ventricle LV as shown in FIG. 14. In an embodiment, catheter 1450 is advanced approximately 5 mm into the left ventricle LV.

Figure 15:
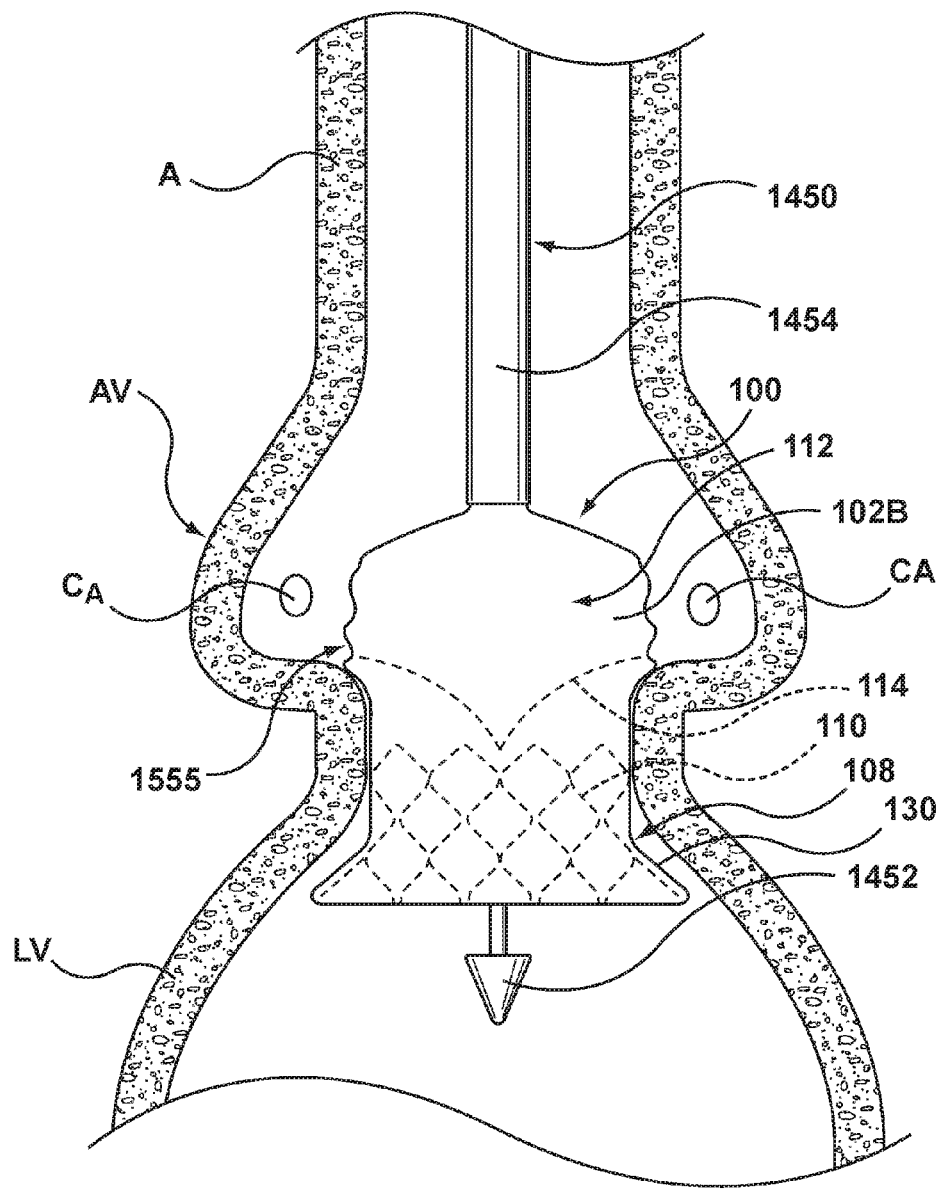
FIG. 15 depicts another step of a method for implanting the valve prosthesis of FIG. 1, wherein an outer sheath of the catheter is retracted to release the first tubular scaffold and intermediate portion of the valve prosthesis.

Once catheter 1450 is positioned as desired, outer sheath 1454 of catheter 1450 is retracted to expose first anchoring segment 108 (and thus first tubular scaffold 110) and at least a portion of central valve segment 112 of prosthesis 100. Once released from outer sheath 1454, self-expanding first tubular scaffold 110 returns to its expanded or deployed configuration as shown in FIG. 15. Upon release from outer sheath 1454, intermediate portion 102B of fabric tubular body 102 which houses prosthetic valve component 114 may include slack 1555 in which the material thereof is baggy, saggy, or otherwise loose. Slack 1555 may be present since intermediate portion 102B is not supported by any tubular or circumferential scaffold elements. Further, upon release from outer sheath 1454, flared end 130 of first tubular scaffold 110 is slightly spaced apart from native aortic valve AV. At this point in the procedure, second tubular scaffold 120 is still restrained within outer sheath 1454.

Figure 16:
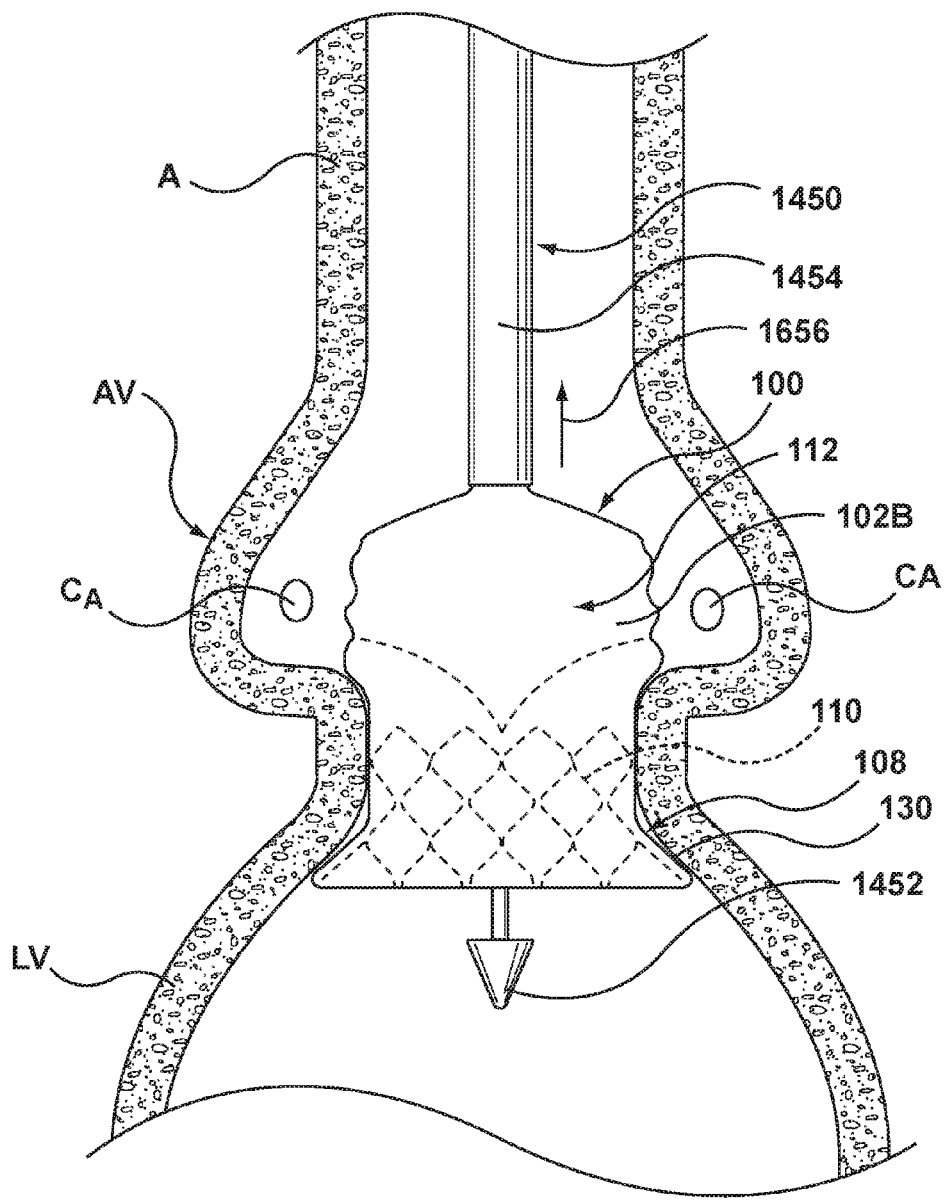
FIG. 16 depicts another step of a method for implanting the valve prosthesis of FIG. 1, wherein the catheter is proximally retracted to seat the first tubular scaffold of the valve prosthesis against the native aortic valve annulus.
Figure 17:
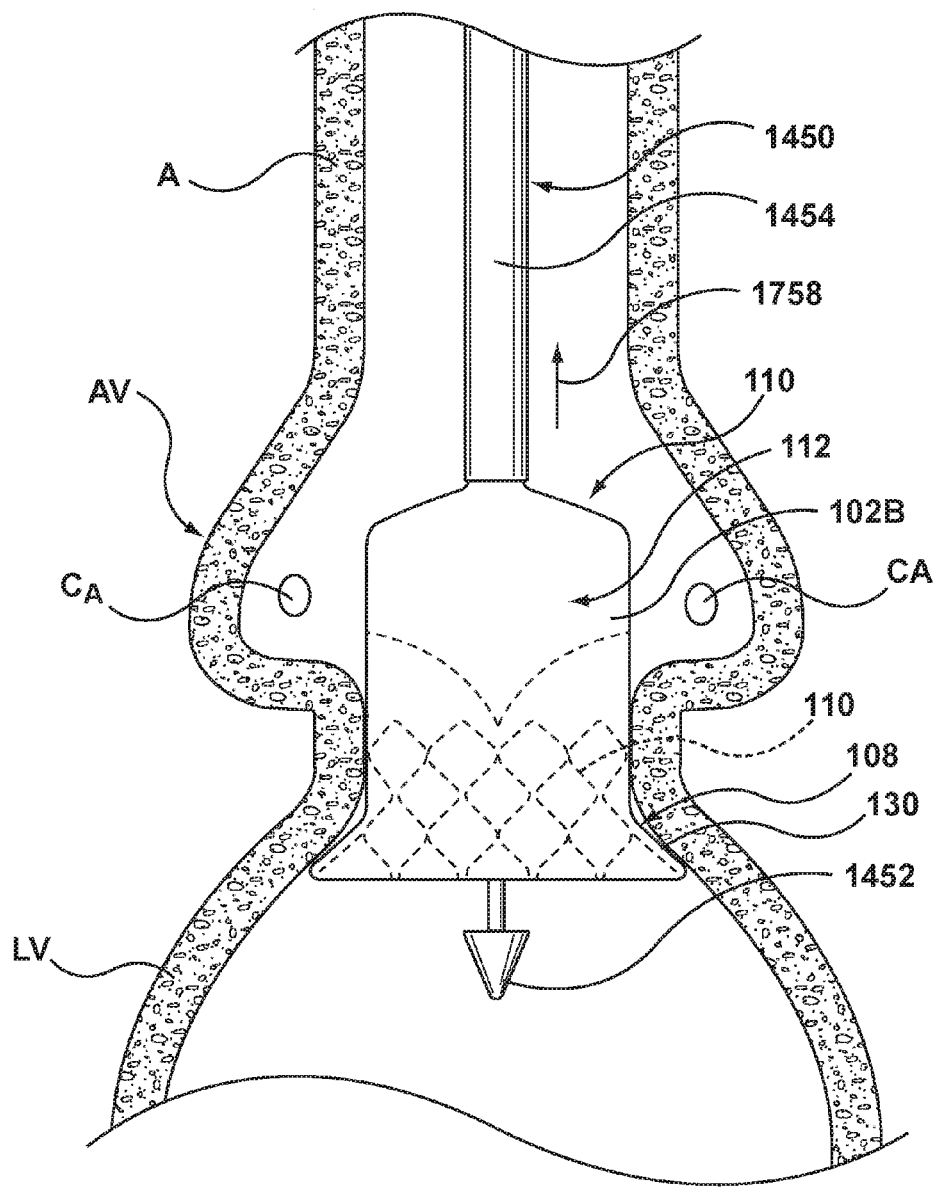
FIG. 17 depicts another step of a method for implanting the valve prosthesis of FIG. 1, wherein the catheter is proximally retracted to stretch or pull taut the intermediate portion of the valve prosthesis.

Referring to FIG. 16, catheter 1450 is then proximally retracted as indicated by directional arrow 1656 in order to seat flared end 130 of first tubular scaffold 110 against the annulus of the native aortic valve AV. The entire catheter 1450 having valve prosthesis 100 mounted thereon may be pulled or proximally retracted by the user, or the catheter may include a separate mechanism (not shown) such that valve prosthesis 100 may be separately or independently pulled or proximally retracted without retracting the entire catheter 1450. With flared end 130 of first tubular scaffold 110 seated in apposition with the annulus of native aortic valve AV, catheter 1450 is further proximally retracted as indicated by directional arrow 1758 in order to supply tension to intermediate portion 102B of tubular fabric body 102 as shown in FIG. 17. Catheter 1450 is pulled proximally until intermediate portion 102B of tubular fabric body 102 is taut or stretched to a generally straight configuration and no slack is present along the length of intermediate portion 102B.

Figure 18:
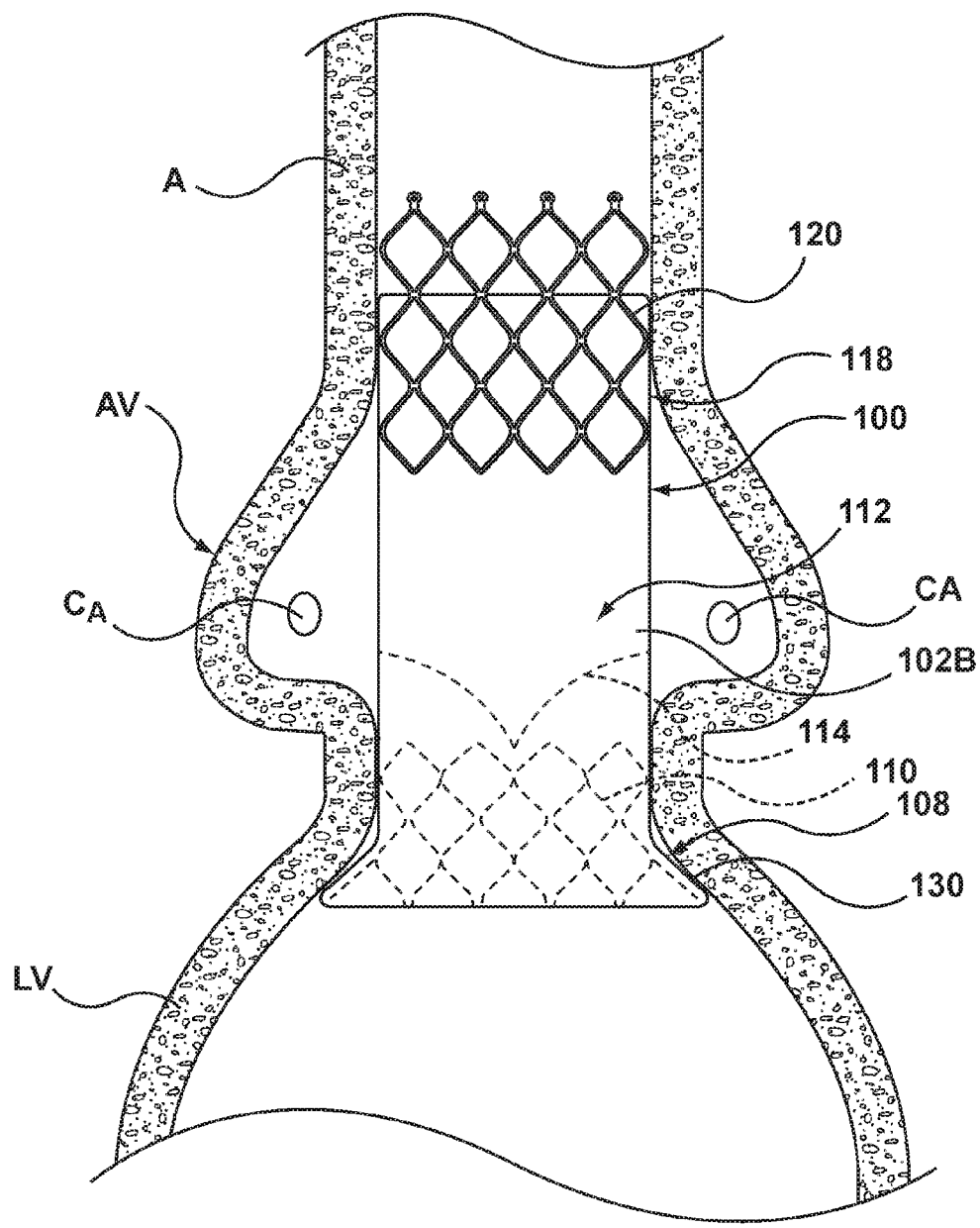
FIG. 18 depicts another step of a method for implanting the valve prosthesis of FIG. 1, wherein an outer sheath of the catheter has been retracted to release the second tubular scaffold and the catheter has been removed, leaving the deployed valve prosthesis implanted at the treatment site.

After intermediate portion 102B of tubular fabric body 102 is taut, outer sheath 1454 of catheter 1450 is retracted to expose second anchoring segment 118 (and thus second tubular scaffold 120). Once released from outer sheath 1454, self-expanding second tubular scaffold 120 returns to its expanded or deployed configuration. Second tubular scaffold 120 deploys against the aorta A, thereby anchoring valve prosthesis 100 to the aortic wall. Catheter 1450 is then removed and valve prosthesis 100 remains deployed within the native aortic valve AV as shown in FIG. 18. After deployment, tension is present between first and second tubular scaffolds and the tension is sufficient to maintain the seal at the aortic annulus during the full cardiac cycle and also holds tubular fabric body 102 taut to maintain a generally straight configuration and proper valve function during the cardiac cycle. If the native aortic valve AV includes native valve leaflets (not shown in FIGS. 14-18) and such leaflets have not been removed or excised, valve prosthesis 100 is deployed within the native valve leaflets of the patient's defective valve, retaining the native valve leaflets in a permanently open state.

Figure 19:
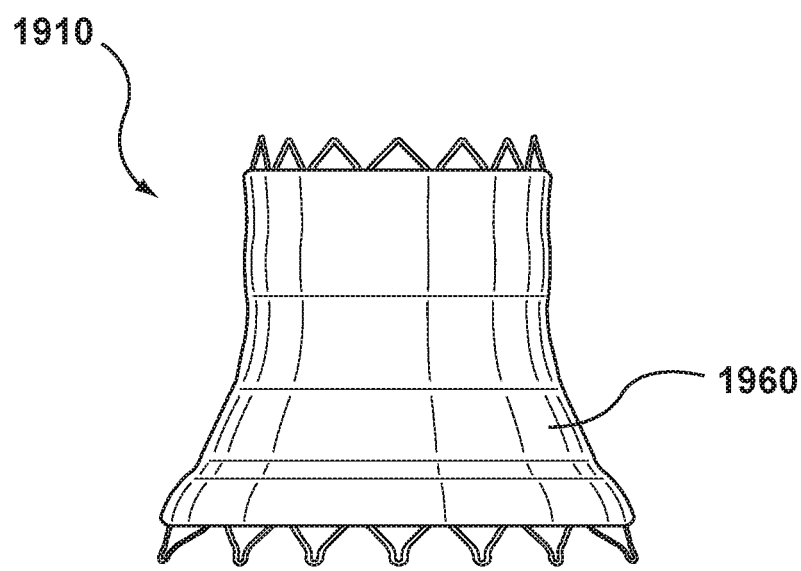
FIG. 19 depicts a first tubular scaffold according to another embodiment hereof, wherein the first tubular scaffold includes a skirt and is shown in an expanded configuration.

In any embodiment hereof, a skirt or other sealing material may be coupled to the first tubular scaffold. As previously described, when configured as a replacement for an aortic valve, the first anchoring segment of valve prosthesis functions as an inflow end of the valve prosthesis and extends into and anchors within the aortic annulus of a patient's left ventricle. The native valve annulus may include surface irregularities on the inner surface thereof, and as a result one or more gaps or cavities/crevices may be present or may form between the perimeter of the valve prosthesis and the native valve annulus. For example, calcium deposits may be present on the native valve leaflets (e.g., stenotic valve leaflets) and/or shape differences may be present between the native heart annulus and the valve prosthesis. More particularly, in some cases native annuli are not perfectly rounded and have indentations corresponding to the commissural points of the native valve leaflets. As a result, a prosthesis having an approximately circular shape does not provide an exact fit in a native valve. These surface irregularities, whatever their underlying cause, can make it difficult for conventional prosthetic valves to form a blood tight seal between the prosthetic valve and the inner surface of the valve annulus, causing undesirable paravalvular leakage and/or regurgitation at the implantation site. FIG. 19 illustrates a side view of a first tubular scaffold 1910 according to another embodiment hereof in which the first tubular scaffold includes a skirt 1960. Skirt 1960 functions to occlude or fill gaps between the perimeter of a valve prosthesis and the native valve annulus, thereby reducing, minimizing, or eliminating leaks there-through. Skirt 1960 extends around an outer or exterior surface of first tubular scaffold 1910 to block blood flow around the outer perimeter of the valve prosthesis (not shown in FIG. 19), thereby minimizing and/or eliminating any paravalvular leakage at the implantation site. In this embodiment, when assembled into a transcatheter valve prosthesis, first scaffold 1910 is coupled to an outer surface of a tubular fabric body (not shown in FIG. 19) such that first scaffold 1910 is sandwiched between the tubular fabric body on the inner surface thereof and skirt 1960 on the outer surface thereof. When deployed, skirt 1960 may be positioned in situ at the native valve annulus, slightly above the valve annulus, slightly below the valve annulus, or some combination thereof. The length of skirt 1960 may vary according to application and skirt 1960 may be shorter or longer than shown. For example, in another embodiment hereof, skirt 1960 extends beyond a proximal end of first scaffold 1910 such that, when assembled into a transcatheter valve prosthesis, skirt 1960 overlays the tubular fabric body at the location of the prosthetic valve component. Suitable materials for skirt 1960 include but are not limited to a low-porosity woven fabric, such as polyester, Dacron fabric, or PTFE. Porous materials advantageously provide a medium for tissue ingrowth, and bioabsorbable materials and/or polyurethane foam with low density and optimal porosity promote sealing of the device to the anatomy. Further, skirt 1960 may be pericardial tissue or may be a knit or woven polyester, such as a polyester or PTFE knit, both of which provide a medium for tissue ingrowth and have the ability to stretch to conform to a curved surface. Polyester velour fabrics may alternatively be used, such as when it is desired to provide a medium for tissue ingrowth on one side and a smooth surface on the other side.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A transcatheter valve prosthesis, the prosthesis comprising:
    a tubular fabric body formed from a synthetic material, the tubular fabric body having a first end portion, a second end portion and an intermediate portion extending between the first and second end portions, wherein the tubular fabric body defines a lumen there-through;
    a first tubular scaffold attached to the tubular fabric body along the first end portion thereof;
    a second tubular scaffold attached to the tubular fabric body along the second end portion thereof, wherein the first and second tubular scaffolds are independent from each other;
    a prosthetic valve component disposed within and secured to the intermediate portion of the tubular fabric body, the prosthetic valve component being configured to block blood flow in one direction to regulate blood flow through the lumen of the tubular fabric body, wherein the prosthetic valve component includes at least two leaflets and at least two commissures, each commissure being formed by attached adjacent lateral ends of an adjoining pair of the at least two leaflets; and
    at least two reinforcement members that are attached to the intermediate portion of the tubular fabric body, wherein each of the at least two reinforcement members is aligned with a respective commissure of the at least two leaflets of the prosthetic valve component, and each of the at least two reinforcement members is a U-shaped segment having a first end adjacent to the first tubular scaffold, a second end adjacent to the first tubular scaffold, a first straight portion extending from the first end and longitudinally oriented along the respective commissure, a second straight portion extending from the second end and longitudinally oriented along the respective commissure, and a curved portion opposing the first and second ends and formed between the first and second straight portions,
    wherein the intermediate portion of the tubular fabric body includes an unsupported portion that is not surrounded by a tubular scaffold such that the unsupported portion of the intermediate portion of the tubular fabric body has no radial support along its length or circumference, and
    wherein at least two windows are formed through the intermediate portion of the tubular fabric body, with the at least two windows being circumferentially positioned relative to the at least two commissures of the prosthetic valve component such that a window is disposed between adjacent commissures, and
    wherein the prosthesis has a compressed configuration for percutaneous delivery within a vasculature and an expanded configuration for deployment within a native valve.

2. The prosthesis of claim 1, wherein the first and second tubular scaffolds have diamond-shaped openings that are laser-cut into the tubular scaffolds and are configured to be self-expanding and are sized to anchor the prosthesis against native valve tissue when the prosthesis is in the expanded configuration.

3. The prosthesis of claim 1, wherein the second tubular scaffold extends beyond the second end portion of the tubular fabric body.

4. The prosthesis of claim 1, wherein the second tubular scaffold is configured to have a higher radial force than the first tubular scaffold.

5. The prosthesis of claim 1, wherein the second tubular scaffold includes barbs on an outer surface thereof.

6. The prosthesis of claim 1, wherein the first tubular scaffold is flared such that a first end of the first tubular scaffold has a smaller diameter than a second end of the first tubular scaffold.

7. The prosthesis of claim 1, wherein the first tubular scaffold is coupled to an outer surface of the tubular fabric body and a skirt is coupled to an outer surface of the first tubular scaffold such that the first tubular scaffold is sandwiched between the tubular fabric body and the skirt.

8. The prosthesis of claim 1, wherein when the prosthesis is in the expanded configuration each of the first tubular scaffold, the intermediate portion of the tubular fabric body and the second tubular scaffold comprises a respective third of a total length of the prosthesis.

9. The prosthesis of claim 1, wherein the at least two reinforcement members are not attached to the first tubular scaffold or the second tubular scaffold.

10. The prosthesis of claim 1, wherein the at least two reinforcement members extend from the first tubular scaffold.

11. A transcatheter valve prosthesis for implantation within a native valve, the prosthesis comprising:
    a tubular fabric body having a first end portion, a second end portion, and an intermediate portion that longitudinally extends between the first and second end portions, wherein the tubular fabric body defines a lumen there-through;
    a first tubular scaffold attached to the tubular fabric body along the first end portion thereof;
    a second tubular scaffold attached to the tubular fabric body along the second end portion thereof, wherein the first and second tubular scaffolds are configured to be self-expanding and are sized to deploy against native valve tissue, the first and second tubular scaffolds being independent from each other;

a prosthetic valve component disposed within and secured to the intermediate portion of the tubular fabric body, the prosthetic valve component being configured to block blood flow in one direction to regulate blood flow through the lumen of the tubular fabric body, wherein the prosthetic valve component includes three leaflets and three commissures, each commissure being formed by attached adjacent lateral ends of an adjoining pair of the three leaflets; and three reinforcement members that are attached to the intermediate portion of the tubular fabric body, wherein each of the three reinforcement members is aligned with a respective commissure of the three leaflets of the prosthetic valve component and each of the three reinforcement members is a U-shaped segment having a first end adjacent to the first tubular scaffold, a second end adjacent to the first tubular scaffold, a first straight portion extending from the first end and longitudinally oriented along the respective commissure, a second straight portion extending from the second end and longitudinally oriented along the respective commissure, and a curved portion opposing the first and second ends and formed between the first and second straight portions, wherein the intermediate portion of the tubular fabric body includes an unsupported portion such that neither of the first or second tubular scaffolds surround the unsupported portion of the tubular fabric body, and wherein three windows are formed through the intermediate portion of the tubular fabric body, wherein the three windows are circumferentially positioned relative to the three commissures of the prosthetic valve component such that a window is disposed between adjacent commissures, and wherein the prosthesis has a compressed configuration for percutaneous delivery within a vasculature and an expanded configuration for deployment within a native valve.

12. The prosthesis of claim 11, wherein the three reinforcement members are not attached to the first tubular scaffold or the second tubular scaffold.

13. The prosthesis of claim 11, wherein the three reinforcement members extend from the first tubular scaffold.

14. The prosthesis of claim 11, wherein the second tubular scaffold is configured to have a higher radial force than the first tubular scaffold.

* * * * *